United States Patent
Matsunaga et al.

(10) Patent No.: US 7,972,389 B2
(45) Date of Patent: Jul. 5, 2011

(54) SECOND PART COMPOSITION FOR HAIR DYEING OR BLEACHING

(75) Inventors: Kenichi Matsunaga, Sumida-ku (JP); Takashi Matsuo, Sumida-ku (JP); Hajime Miyabe, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/811,020

(22) PCT Filed: Dec. 26, 2008

(86) PCT No.: PCT/JP2008/003994
§ 371 (c)(1),
(2), (4) Date: Jun. 28, 2010

(87) PCT Pub. No.: WO2009/084219
PCT Pub. Date: Jul. 9, 2009

(65) Prior Publication Data
US 2010/0281627 A1 Nov. 11, 2010

(30) Foreign Application Priority Data
Dec. 28, 2007 (JP) .................................. 2007-338838

(51) Int. Cl.
*A61Q 5/10* (2006.01)

(52) U.S. Cl. ............. 8/405; 8/431; 8/435; 8/540; 8/597; 8/604

(58) Field of Classification Search ............. 8/405, 431, 8/435, 540, 597, 604
See application file for complete search history.

(56) References Cited

U.S. PATENT DOCUMENTS
2007/0157399 A1 * 7/2007 Nobuto et al. .................... 8/405

FOREIGN PATENT DOCUMENTS

| | | |
|---|---|---|
| EP | 1 714 677 | 10/2006 |
| EP | 1 897 532 | 3/2008 |
| JP | 1 213220 | 8/1989 |
| JP | 2003 221319 | 8/2003 |
| JP | 2004 269503 | 9/2004 |
| JP | 2006 28107 | 2/2006 |
| JP | 2006 182685 | 7/2006 |
| JP | 2007 191458 | 8/2007 |
| JP | 2008 19185 | 1/2008 |
| JP | 2008 31056 | 2/2008 |
| WO | 03 089330 | 10/2003 |

OTHER PUBLICATIONS

STIC Search Report dated Nov. 9, 2010.*

* cited by examiner

*Primary Examiner* — Eisa B Elhilo
(74) *Attorney, Agent, or Firm* — Oblon, Spivak, McClelland, Maier & Neustadt, L.L.P.

(57) ABSTRACT

Provided is a second part composition for hair dyeing or bleaching, which is mixed with a first part composition containing an alkali agent before use, the composition containing the following components (A) to (D): (A) an organic amine having at least one hydrophobic chain or a salt thereof; (B) an oily component which is a liquid form at 25° C. under normal pressure (1013.25 hPa); (C) an oxidizing agent; and (D) water, in which the composition has a pH of 1 to 6 at 25° C.

15 Claims, No Drawings

SECOND PART COMPOSITION FOR HAIR DYEING OR BLEACHING

FIELD OF THE INVENTION

The present invention relates to a second part composition for hair dyeing or bleaching used by being mixed with a first part composition containing an alkali agent.

BACKGROUND OF THE INVENTION

An alkali agent blended into a first part in an oxidizing hair dye or bleaching agent is used for improving a bleaching effect and a hair dyeing effect, and activating an activity of an oxidizing agent blended into a second part to promote the oxidative degradation of melanin granules in hair so that a bright color tone may be obtained. Although ammonia has been generally used as the alkali agent, ammonia has a strong pungent odor. Attempts have been made to use, for example, alkanolamines instead of ammonia in order to reduce the pungent odor of ammonia (see, for example, Patent Document 1). However, the alkanolamines involve some problems, in that, the alkanolamines also have their unique unpleasant odors, and do not have enough bleaching performance for providing hair with a bright tinge. Therefore, an oxidizing hair dye or bleaching agent which enables not only to prevent generation of pungent odor or unpleasant odor but also to provide bleaching performance sufficient for providing hair with a bright tinge has been desired.
[Patent Document 1] JP-A-01-213220

SUMMARY OF THE INVENTION

The present invention provides a second part composition for hair dyeing or bleaching, which is mixed with a first part composition containing an alkali agent before use, the composition containing the following components (A) to (D): (A) an organic amine having at least one hydrophobic chain or a salt thereof; (B) an oily component which is a liquid form at 25° C. under normal pressure (1013.25 hPa); (C) an oxidizing agent; and (D) water, in which the composition has a pH of 1 to 6 at 25° C.

Further, the present invention provides a kit for hair dyeing or bleaching, including: a first part composition for hair dyeing or bleaching containing an alkali agent; and the above-mentioned second part composition for hair dyeing or bleaching, in which a composition obtained by mixing the first part and the second part has a pH of 8 to 12 at 25° C.

In addition, the present invention provides a method for hair dyeing or bleaching, the method including: mixing the above-mentioned second part composition with a first part composition for hair dyeing or bleaching containing an alkali agent; and applying the mixture to hair.

DETAILED DESCRIPTION OF THE INVENTION

The present invention relates to a second part composition for hair dyeing or bleaching from which generation of pungent odor or unpleasant odor at the time of its application is suppressed and which exerts sufficient bleaching performance.

The inventors of the present invention have found that the above-mentioned problems can be solved by blending a specific organic amine or a salt thereof into a second part composition for hair dyeing or bleaching, together with a liquid oily component. That is, in an acidic second part, the organic amine transforms into a cationic surfactant form and functions as an emulsifier. However, when the second part is mixed with a first part and the mixture has an alkaline pH, the above-mentioned cationic surfactant reverts to the original amine, and its surface activity is lost. As a result, the emulsion structure of the second part is destroyed, and the oily component is released to a liquid-air interface in an oil film fashion. Accordingly, the volatilization of an alkali agent can be prevented, and a pungent odor or unpleasant odor is prevented.

[Component (A): Organic Amine]

Among the organic amine having at least one hydrophobic chain or the salt of the amine as the component (A), the hydrophobic chain is preferably a linear or branched alkyl or alkenyl group having 6 to 24, more preferably 12 to 24, or even more preferably 14 to 22, carbon atoms. The organic amine is more preferably represented by the following general formula (1).

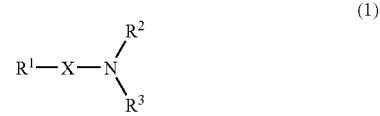

[wherein $R^1$ represents a linear or branched alkyl or alkenyl group having 6 to 24 carbon atoms, $R^2$ and $R^3$ may be the same or different from each other and each represent an alkyl group having 1 to 6 carbon atoms or $-(AO)_nH$ (A represents an alkylene group having 2 to 4 carbon atoms, n represents a number of 1 to 6, and n A's may be the same or different from each other and may be arranged in an arbitrary fashion), and X represents a single bond, $-O-(CH_2)_m-$, $-C(O)-NH-(CH_2)_m-$, $-NH-C(O)-(CH_2)_m-$, or $-[O-CH_2-CH(OH)-CH_2]_l-$ (m represents a number of 2 to 4 and l represents a number of 1 to 5).]

In the above general formula (I), $R^1$, $R^2$, and $R^3$ are preferably the following groups from such a viewpoint that the dispersibility of the component (B) is improved under an acidic condition so that the emulsion stability of the second part may be improved, and such a viewpoint that the component (B) is quickly released from an emulsion state after the mixing with the first part.

$R^1$ is preferably a linear or branched alkyl or alkenyl group, or more preferably alkyl group, having 12 to 24, or more preferably 14 to 22, carbon atoms. $R^2$ and $R^3$, which may be the same or different from each other, are each preferably an alkyl group having 1 to 6 carbon atoms or a $-(CH_2CH_2O)_nH$ group (n represents 1 to 3, or more preferably 1). When one of $R^2$ and $R^3$ is a $-(CH_2CH_2O)_nH$ group, the other is preferably an alkyl group having 1 to 6 carbon atoms. Further, both $R^2$ and $R^3$ are preferably alkyl groups each having 1 to 6 carbon atoms which are the same or different from each other, or more preferably each a methyl group or an ethyl group. Examples of the salt include: inorganic acid salts such as a hydrochloride and a phosphate; and organic acid salts such as a citrate, a glycolate, and a lactate. Organic amine or the salt thereof as the component (A) can be used alone, or two or more kinds of them can be used in combination.

The amount of the organic amine or the salt of the amine as the component (A) is preferably 0.1 to 20% by mass, more preferably 0.5 to 15% by mass, or even more preferably 1 to 10% by mass in the second part composition of the present invention in terms of the organic amine.

[Component (B): Oily Component]

The oily component which is a liquid form at 25° C. under normal pressure (1013.25 hPa) as the component (B) is blended for preventing generation of a pungent odor or unpleasant odor at the time of the application, for improving the bleaching performance, and for providing finished hair with moisture. Examples of such oily component include hydrocarbon oils, animal and vegetable oils, higher alcohols, higher fatty acids, ester oils, and silicone oils. Examples of the hydrocarbon oils include α-olefin oligomer, light isoparaffin, light liquid isoparaffin, squalane, polybutene, liquid isoparaffin, and liquid paraffin. Examples of the animal and vegetable oils include olive oil, Camellia japonica seed oil, Camellia sinensis seed oil, Camellia kissi oil, safflower oil, sunflower oil, soybean oil, cottonseed oil, sesame oil, corn oil, peanut oil, rapeseed oil, rice bran oil, rice germ oil, wheat germ oil, Job's tears oil, grapeseed oil, almond oil, avocado oil, carrot oil, macadamia nut oil, castor oil, linseed oil, coconut oil, mink oil, yolk oil, and jojoba oil. Examples of the higher alcohols include isostearyl alcohol, 2-octyl dodecanol, decyl tetradecanol, oleyl alcohol, 2-hexyl decanol, linoleyl alcohol, and linolenyl alcohol. Examples of the higher fatty acids include isostearic acid, oleic acid, and linoleic acid. Examples of the ester oils include diisopropyl adipate, diisobutyl adipate, dioctyl adipate, di-2-hexyldecyl adipate, diisostearyl adipate, isostearyl myristate, isotridecyl myristate, isopropyl myristate, octyldodecyl myristate, cetyl octanoate, isononyl isononanoate, isodecyl isononanoate, isotridecyl isononanoate, diisopropyl sebacate, isopropyl palmitate, hexyl laurate, decyl oleate, hexyldecyl dimethyloctanoate, octyl palmitate, lauryl lactate, octyldodecyl lactate, isocetyl stearate, isocetyl isostearate, ethylene glycol dioctanoate, dipentaerythritol fatty acid ester, cetyl caprate, glyceryl tricaprylate, neopentyl glycol dicaprate, and diisostearyl malate. Examples of the silicone oils include methyl polysiloxane, methylphenyl polysiloxane, methyl cyclopolysiloxane, polyether modified silicone, amino modified silicone, betaine modified silicone, alkyl modified silicone, and alkoxy modified silicone. Each of those oily components may be used alone, or two or more kinds of them may be used in combination.

The amount of the oily component as the component (B) is preferably 0.1 to 50% by mass, more preferably 1 to 40% by mass, even more preferably 2 to 30% by mass, or even further more preferably 5 to 20% by mass in the second part composition of the present invention.

[Component (C): Oxidizing Agent]

Examples of the oxidizing agent as the component (C) include hydrogen peroxide, and urea peroxide, melamine peroxide, sodium perborate, potassium perborate, sodium percarbonate, and potassium percarbonate as hydrogen peroxide generators. Of those, hydrogen peroxide is preferred. The amount of the oxidizing agent is preferably 0.1 to 12% by mass, more preferably 0.5 to 9% by mass, or even more preferably 1 to 6% by mass in the second part composition of the present invention in terms of hydrogen peroxide, from the viewpoint of a sufficient bleaching/hair dyeing effect, and the reductions of hair damage and scalp irritation.

[Surfactant]

The second part composition of the present invention can be blended with any supplemental cationic surfactant or nonionic surfactant other than the cationic surfactant formed of the organic amine as the component (A) under an acidic condition.

Examples of the cationic surfactant include lauryltrimethylammonium chloride, cetyltrimethylammonium chloride, stearyltrimethylammonium chloride, behenyltrimethylammonium chloride, distearyldimethylammonium chloride, cetyltrimethylammonium bromide, and stearyltrimethylammonium bromide. Each of those cationic surfactants can be used alone, or two or more kinds of them can be used in combination.

Examples of the nonionic surfactant include polyoxyethylene (hereinafter referred to as "POE") alkyl ethers, POE alkyl phenyl ethers, POE/polyoxypropylene (hereinafter referred to as "POP") alkyl ethers, POE sorbitan fatty acid esters, POE fatty acid esters, POE hydrogenated castor oil, and fatty acid glycerin esters. Of those, the POE alkyl ethers, the POE alkyl phenyl ethers, the POE/POP alkyl ethers, and the like are preferred because of their resistance to acids and alkali agents, and the POE alkyl ethers are more preferred. Specific examples of the POE alkyl ethers include POE lauryl ether, POE cetyl ether, POE stearyl ether, POE behenyl ether, and POE tridecyl ether. Each of those nonionic surfactants can be used alone, or two or more kinds of them can be used in combination.

These supplemental surfactants are preferably not blended, from the viewpoint that a function of the component (A) is preferable to be sufficiently exerted for causing demulsification at the time of the mixing of the first part and the second part so that an oil film may be formed. However, if such a supplemental surfactant is blended for improving the stability of the second part, the amount is preferable to be limited up to the amount that the demulsification is not inhibited at the time of the mixing of the first part and the second part and hence the oil film can be formed. Specifically, the content of such a supplemental surfactant is preferably 0.01 to 10% by mass, more preferably 0.05 to 5% by mass, or even more preferably 0.1 to 3% by mass in the second part of the present invention. The ratio of such a supplemental surfactant is preferably 50 parts by mass or less, more preferably 30 parts by mass or less, or even more preferably 10 parts by mass or less with respect to 100 parts by mass of the component (A) in terms of the organic amine.

[Medium]

Water and, if required, an organic solvent are used as a medium for the second part composition of the present invention. Examples of the organic solvent include: lower alkanols such as ethanol and 2-propanol; polyhydric alcohols such as propylene glycol and 1,3-butylene glycol; aromatic alcohols such as benzyl alcohol, benzyloxy ethanol, and phenoxy ethanol; cellosolves such as ethyl cellosolve and butyl cellosolve; and carbitols such as ethyl carbitol and butyl carbitol.

[Other Optional Components]

Any other components typically used as raw materials for cosmetics, in addition to the above-mentioned components, can be added to the second part composition of the present invention. Examples of such optional components include natural or synthetic polymers, hydrolyzed proteins, amino acids, antiseptics, chelating agents, stabilizers, antioxidants, plant extracts, vitamins, thickeners, perfumes, and UV absorbers.

[Dosage Form]

The form of the second part composition of the present invention can be, for example, an emulsion form, a cream form, a gel form, or a paste form.

[pH]

The second part composition of the present invention has a pH of 1 to 6, or preferably 2 to 4 at 25° C. Examples of pH adjustor are, for example, an inorganic acid such as hydrochloric acid or phosphoric acid, or a salt thereof, or an organic acid such as citric acid, glycolic acid, or lactic acid, or a salt thereof.

[Use]

The second part composition of the present invention is used as an oxidizing agent composition for a two- or three-part oxidizing hair dye or hair bleaching agent that has been widely used. That is, a two-component hair dye composition or hair bleaching agent can be prepared by combining the second part composition of the present invention with the first part containing the alkali agent. Alternatively, a three-component hair dye composition or hair bleaching agent can be prepared by further combining a third part as a powdery oxidizing agent formed of a granulated product of, for example, a persulfate (such as ammonium persulfate, potassium persulfate, or sodium persulfate).

First Part

When the above-mentioned first part contains a dye, a two-part hair dye composition is provided. When the first part does not contain any dye, a two-part hair bleaching agent is provided. Oxidizing dye intermediates and direct dyes used in ordinary hair dyes can be optionally used as the dye. In addition, examples of the alkali agent include: ammonia; alkanolamines such as monoethanolamine, isopropanolamine, 2-amino-2-methylpropanol, and 2-aminobutanol; alkanediamines such as 1,3-propanediamine; carbonates such as guanidine carbonate, sodium carbonate, potassium carbonate, and ammonium carbonate; and hydrogen carbonates such as sodium hydrogen carbonate, potassium hydrogen carbonate, and ammonium hydrogen carbonate. In addition, the same components as those exemplified for the second part, typically used as raw materials for cosmetics, can each be incorporated into the first part.

The first part has a pH (25° C.) of preferably 8 to 12 or more preferably 9 to 11. In addition, when the second part composition of the present invention is mixed with the first part composition, the pH (25° C.) of the mixture preferably exceed 7 so that the mixture may be alkaline, from the viewpoint that the surface activity of the component (A) blended into the second part is lost so that the emulsion structure of the second part may be destroyed and the component (B) may be released to a liquid-air interface in an oil film fashion. In addition, the pH is preferably 8 to 12 or more preferably 9 to 11 from the viewpoint of a bleaching/hair dyeing effect and skin irritation. In addition, the first part composition and the second part composition can be combined to provide a kit for dyeing or bleaching formed of the compositions.

Treatment Method

Treatment method for hair dying or bleaching with the second part composition of the present invention includes, for example, mixing the second part of the present invention with the first part (and further, the third part in the case of a three-part composition) immediately before use; applying the mixture to the hair; allowing to stand for a predetermined time period; washing out the mixture after the allowing to stand; and drying the hair. The temperature at which the mixture is applied to the hair is 15 to 45° C., and the time period for which the mixture is applied to the hair is preferably 3 to 45 minutes, more preferably 5 to 30 minutes, or even more preferably 10 to 30 minutes.

EXAMPLES

Examples 1 to 8 and Comparative Examples 1 to 6

First parts (for hair dyeing and bleaching) having the following formulations, and second parts (Inventive product 1 to 4 and Comparative Products 1 to 3) shown in Table 1 were prepared. Then, "pungent odor" and "color brightness" or "dyeing performance" of combinations shown in Table 2 (hair dyes) and Table 3 (bleaching agents) when the parts were used for mixing were evaluated The evaluation was performed by ten panelists, and the total points are shown in Tables 2 and 3.

| First part for hair dyeing | |
|---|---|
| | (% by mass) |
| Toluene-2,5-diamine | 0.4 |
| p-Aminophenol | 0.6 |
| m-Aminophenol | 0.3 |
| Resorcin | 0.6 |
| Stearyltrimethylammonium chloride (28% by mass) | 3.0 |
| Polyoxyethylene (2) cetyl ether | 0.5 |
| Polyoxyethylene (40) cetyl ether | 2.0 |
| Stearyl alcohol | 6.0 |
| Oleyl alcohol | 1.0 |
| Propylene glycol | 5.0 |
| Ascorbic acid | 0.5 |
| Aqueous ammonia (28% by mass) | 8.0 |
| Purified water | Balance |
| pH (25° C.) = 11 | |

| First part for bleaching | |
|---|---|
| | (% by mass) |
| Stearyltrimethylammonium chloride (28% by mass) | 3.0 |
| Polyoxyethylene (2) cetyl ether | 0.5 |
| Polyoxyethylene (40) cetyl ether | 2.0 |
| Stearyl alcohol | 6.0 |
| Oleyl alcohol | 1.0 |
| Propylene glycol | 5.0 |
| Ascorbic acid | 0.5 |
| Aqueous ammonia (28% by mass) | 8.0 |
| Purified water | Balance |
| pH (25° C.) = 11 | |

TABLE 1

| | | Inventive Product | | | | Comparative Product | | |
|---|---|---|---|---|---|---|---|---|
| Second part (% by mass) | | 1 | 2 | 3 | 4 | 1 | 2 | 3 |
| (A) | Compound (I) | 3 | — | — | — | — | — | 3 |
| | Compound (II) | — | 3 | — | — | — | — | — |
| | Compound (III) | — | — | 3 | — | — | — | — |
| | Compound (IV) | — | — | — | 3 | — | — | — |
| (A)' | Behenyltrimethyl ammonium chloride (80 wt %) | — | — | — | — | 3 | 3 | — |
| | Behenyl alcohol | 5 | 5 | 5 | 5 | 5 | 5 | 5 |
| | Stearyl alcohol | 2 | 2 | 2 | 2 | 2 | 2 | 2 |

TABLE 1-continued

|  |  | Inventive Product | | | | Comparative Product | | |
|---|---|---|---|---|---|---|---|---|
| Second part (% by mass) | | 1 | 2 | 3 | 4 | 1 | 2 | 3 |
| (B) | Liquid paraffin | 10 | 10 | 10 | 10 | 10 | — | — |
|  | Glycerin | 6 | 6 | 6 | 6 | 6 | 6 | 6 |
|  | Oxyquinoline sulfate | 0.05 | 0.05 | 0.05 | 0.05 | 0.05 | 0.05 | 0.05 |
|  | Phosphoric acid | Adjusted to pH 3.5 (25° C.) | | | | | | |
| (C) | Aqueous hydrogen peroxide (35 wt %) | 16 | 16 | 16 | 16 | 16 | 16 | 16 |
| (D) | Purified water | Balance | Balance | Balance | Balance | Balance | Balance | Balance |

Compound ( I )
$CH_3(CH_2)_{17}O(CH_2)_3N(CH_3)_2$
Compound ( II )

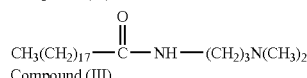

Compound (III)

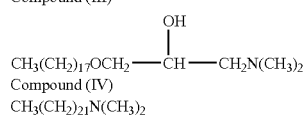

Compound (IV)
$CH_3(CH_2)_{21}N(CH_3)_2$

[Evaluation Methods]
(1) Pungent Odor

The first part and the second part prepared in amounts of 5 g each were sufficiently mixed, and then an aliquot of the mixture was applied to a dish having a diameter of 7 cm. Sensory evaluation was performed by smelling the applied mixture and scoring according to the following five levels, in comparison with Comparative Example 1 (in the case of a composition for hair dyeing) or Comparative Example 4 (in the case of a composition for bleaching) as a control.

+2: The pungent odor is weak compared with that of Comparative Example 1 (or 4).
+1: The pungent odor is somewhat weak compared with that of Comparative Example 1 (or 4).
±0: The pungent odor is substantially comparable to that of Comparative Example 1 (or 4).
−1: The pungent odor is somewhat strong compared with that of Comparative Example 1 (or 4).
−2: The pungent odor is strong compared with that of Comparative Example 1 (or 4).

(2) Dyeing Performance

The first part and the second part prepared in amounts of 1 g each were sufficiently mixed. The mixture was applied to a white hair tress (1 g of Chinese hair), and was then incubated for 20 minutes. The hair was rinsed with flowing water, washed with a shampoo, and dried. After that, visual evaluation was performed by scoring according to the following five levels in comparison with Comparative Example 1 as a control.

+2: The dyeing performance is excellent compared with that of Comparative Example 1.
+1: The dyeing performance is somewhat excellent compared with that of Comparative Example 1.
±0: The dyeing performance is substantially comparable to that of Comparative Example 1.
−1: The dyeing performance is somewhat inferior to that of Comparative Example 1.
−2: The dyeing performance is inferior to that of Comparative Example 1.

(3) Color Brightness

The first part and the second part prepared in amounts of 10 g each were sufficiently mixed. The mixture was applied to a black hair tress (15 g of Japanese hair), and was then incubated for 20 minutes. The hair was rinsed with flowing water, washed with a shampoo, and dried. After that, visual evaluation was performed by scoring according to the following five levels in comparison with Comparative Example 4 as a control.

+2: The color brightness is excellent compared with that of Comparative Example 4.
+1: The color brightness is somewhat excellent compared with that of Comparative Example 4.
±0: The color brightness is substantially comparable to that of Comparative Example 4.
−1: The color brightness is somewhat inferior to that of Comparative Example 4.
−2: The color brightness is inferior to that of Comparative Example 4.

TABLE 2

|  | Example | | | | Comparative Example | | |
|---|---|---|---|---|---|---|---|
|  | 1 | 2 | 3 | 4 | 1 | 2 | 3 |
| First part | First part for hair dyeing | | | | | | |
| Second part | Inventive Product 1 | Inventive Product 2 | Inventive Product 3 | Inventive Product 4 | Comparative Product 1 | Comparative Product 2 | Comparative Product 3 |
| pH (25° C.) at time of mixing | 10 | 10 | 10 | 10 | 10 | 10 | 10 |
| Pungent odor | +20 | +20 | +20 | +20 | — | −14 | −15 |

TABLE 2-continued

|  | Example | | | | Comparative Example | | |
| --- | --- | --- | --- | --- | --- | --- | --- |
|  | 1 | 2 | 3 | 4 | 1 | 2 | 3 |
| Dyeing performance | +11 | +11 | +10 | +10 | — | −10 | −10 |

TABLE 3

|  | Example | | | | Comparative Example | | |
| --- | --- | --- | --- | --- | --- | --- | --- |
|  | 5 | 6 | 7 | 8 | 4 | 5 | 6 |
| First part |  |  |  |  | First part for bleaching |  |  |
| Second part | Inventive Product 1 | Inventive Product 2 | Inventive Product 3 | Inventive Product 4 | Comparative Product 4 | Comparative Product 5 | Comparative Product 6 |
| pH (25° C.) at time of mixing | 10 | 10 | 10 | 10 | 10 | 10 | 10 |
| Pungent odor | +20 | +20 | +20 | +20 | — | −14 | −15 |
| Color brightness | +11 | +10 | +10 | +11 | — | −12 | −10 |

The invention claimed is:

1. A second part composition for hair dyeing or bleaching, which is mixed with a first part composition comprising an alkali agent before use, the second part composition comprising the following components (A) to (D):

(A) an organic amine represented by the following formula (1):

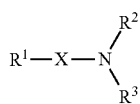

wherein $R^1$ is a linear or branched alkyl or an alkenyl group having 6 to 24 carbon atoms, $R^2$ and $R^3$ are, independently, an alkyl group having 1 to 6 carbon atoms or $-(AO)_nH$, wherein A is an alkylene group having 2 to 4 carbon atoms, n is a number from 1 to 6, and n A's may be the same or different from each other and may be arranged in an arbitrary fashion, and X is a single bond, $-O-(CH_2)_m-$, $-C(O)-NH-(CH_2)_m-$, $-NH-C(O)-(CH_2)_m-$, or $-[O-CH_2-CH(OH)-CH_2]_l-$ wherein m is a number from 2 to 4 and l is a number from 1 to 5, or a salt thereof;

(B) an oily component which is a liquid at 25° C. under normal pressure of 1013.25 hPa;

(C) an oxidizing agent;

(D) water, and (E) optionally, at least one supplemental surfactant different from the component (A);

wherein the second part composition has a pH of 1 to 6 at 25° C., and wherein a ratio of the optional at least one supplemental surfactant to the component (A) is 50 parts by mass of the at least one supplemental surfactant to 100 parts by mass of the component (A).

2. A kit for hair dyeing or bleaching, comprising:
a first part composition for hair dyeing or bleaching comprising an alkali agent; and
the second part composition for hair dyeing or bleaching according to claim 1,
wherein a composition obtained by mixing the first part and the second part has a pH of 8 to 12 at 25° C.

3. A method for hair dyeing or bleaching, comprising:
mixing the second part composition according to claim 1 with a first part composition for hair dyeing or bleaching comprising an alkali agent; and
applying the mixture to hair.

4. The second part composition for hair dyeing or bleaching, according to claim 1, wherein
$R^1$ is an alkyl group having 12 to 24 carbons.

5. The second part composition for hair dyeing or bleaching, according to claim 1, wherein
$R^2$ and $R^3$ are independently an alkyl group having 1 to 6 $(CH_2CH_2O)_nH$ group, wherein n is 1 to 3.

6. The second part composition for hair dyeing or bleaching, according to claim 1, wherein
$R^2$ and $R^3$ are independently a methyl or ethyl group.

7. The second part composition for hair dyeing or bleaching, according to claim 1, wherein a content of the component (A) is from 0.1 to 20% by mass.

8. The second part composition for hair dyeing or bleaching, according to claim 1, wherein
the oily component (B) is at least one selected from the group consisting of a hydrocarbon oil, an animal oil, a vegetable oil, a higher alcohol, a higher fatty acid, an ester oil, and a silicone oil.

9. The second part composition for hair dyeing or bleaching, according to claim 1, wherein a content of the component (B) is from 0.1 to 50% by mass.

10. The second part composition for hair dyeing or bleaching, according to claim 1, wherein the oxidizing agent (C) is selected from the group consisting of hydrogen peroxide, urea peroxide, melamine peroxide, sodium perborate, potassium perborate, sodium percarbonate, and potassium percarbonate.

11. The second part composition for hair dyeing or bleaching, according to claim 10, wherein the oxidizing agent (C) is hydrogen peroxide.

12. The second part composition for hair dyeing or bleaching, according to claim 1, wherein a content of the component (C) is from 0.1 to 50% by mass.

13. The second part composition for hair dyeing or bleaching, according to claim 1, wherein the optional supplemental surfactant is a cationic surfactant or a nonionic surfactant.

14. The second part composition for hair dyeing or bleaching, according to claim 1, further comprising an organic solvent selected from the group consisting of a lower alkanol, a polyhydric alcohol, an aromatic alcohol, a cellosolve and a carbitol.

15. The second part composition for hair dyeing or bleaching, according to claim 1, further comprising a cosmetic component selected from the group consisting of a natural or synthetic polymer, a hydrolyzed protein, an amino acid, an antiseptic, a chelating agent, a stabilizer, an antioxidant, a plant extract, a vitamin a, thickener, a perfume, and a UV absorber.

* * * * *